United States Patent
Balji et al.

(10) Patent No.: US 8,115,101 B2
(45) Date of Patent: Feb. 14, 2012

(54) CABLES FOR PATIENT MONITORING AND RELATED SYSTEMS AND METHODS

(75) Inventors: Jack Balji, Mahwah, NJ (US); Cadathur Rajagopalan, Dumont, NJ (US); Scott Eaton, Briarcliff Manor, NY (US); Joe Petruzzelli, Paramus, NJ (US)

(73) Assignee: Mindray DS USA, Inc., Mahwah, NJ (US)

( * ) Notice: Subject to any disclaimer, the term of this patent is extended or adjusted under 35 U.S.C. 154(b) by 332 days.

(21) Appl. No.: 12/432,558

(22) Filed: Apr. 29, 2009

(65) Prior Publication Data

US 2010/0276195 A1    Nov. 4, 2010

(51) Int. Cl.
*H01R 9/05* (2006.01)
(52) U.S. Cl. .................................... 174/75 C
(58) Field of Classification Search ............ 174/75 C
See application file for complete search history.

(56) References Cited

U.S. PATENT DOCUMENTS

| | | | | |
|---|---|---|---|---|
| 4,974,600 | A * | 12/1990 | Reyes | 600/509 |
| 5,566,680 | A * | 10/1996 | Urion et al. | 600/561 |
| 5,871,451 | A * | 2/1999 | Unger et al. | 600/509 |
| 6,142,949 | A * | 11/2000 | Ubby | 600/508 |
| 6,236,874 | B1 * | 5/2001 | Devlin et al. | 600/372 |
| 6,654,631 | B1 * | 11/2003 | Sahai | 600/509 |
| 6,728,564 | B2 * | 4/2004 | Lahteenmaki | 600/383 |
| 7,112,097 | B1 * | 9/2006 | Lam | 439/654 |
| 7,272,428 | B2 * | 9/2007 | Hopman et al. | 600/382 |
| 7,933,642 | B2 * | 4/2011 | Istvan et al. | 600/509 |
| 2006/0047214 | A1 * | 3/2006 | Fraden | 600/513 |
| 2006/0073728 | A1 * | 4/2006 | Zaiken et al. | 439/488 |

* cited by examiner

*Primary Examiner* — Timothy Thompson
*Assistant Examiner* — Hiram E Gonzalez
(74) *Attorney, Agent, or Firm* — Kory D. Christiansen; Stoel Rives LLP (57) ABSTRACT

Patient monitoring systems can include a cable for transmitting information from a patient parameter sensor to a monitor. The cable can include an electrical circuit that can store information regarding the cable and can communicate information to the monitor.

33 Claims, 6 Drawing Sheets

CABLES FOR PATIENT MONITORING AND RELATED SYSTEMS AND METHODS

TECHNICAL FIELD

The present disclosure relates to cables for use in monitoring patients.

SUMMARY

Embodiments of cables for use in monitoring patients, as well as related systems and methods, are disclosed.

DETAILED DESCRIPTION

Devices for monitoring physiological or other parameters of a patient, such as the patient's blood pressure, cardiac activity, and/or temperature, generally receive information regarding the patient parameters via electrical cables that are connected to sensors positioned near, on, and/or or inside of the patient. Often, the patient may be transferred from one room of a hospital to another, such as from an emergency room to an intensive care unit or from a surgery room to a recovery room. In such instances, it can be desirable to disconnect the cables from one monitoring device and connect them to another. The standard practice for disconnecting and connecting cables in this manner requires a medical practitioner to ensure that each cable is routed from the sensor at or near the patient to the proper port of the new monitor. The cables often become intertwined or jumbled during use, thus this process can be time consuming and prone to errors. This can be problematic in the accuracy-sensitive and often time-sensitive context of patient monitoring.

These and/or other problems can be addressed, ameliorated, or resolved by certain embodiments of cables and related systems and methods, as described herein. In some embodiments, a cable that is configured to transmit information from a sensor to a patient monitoring device can include a circuit that provides the cable with a degree of intelligence. In some embodiments, the circuit stores information pertinent to operation of the cable, such as, for example, the type of physiological sensor with which the cable is configured to be coupled, the date of manufacture of the cable, the total time of active usage of the cable, etc. In other or further embodiments, the circuit can be configured to transition among two or more operational states, each of which can correspond to a different sensor configuration. For example, in some embodiments, the cable can be connected to a transducer that may be able to obtain different forms of invasive blood pressure readings, depending on the placement of a cannula within the patient's vasculature. A practitioner thus can select an appropriate setting for the circuit such that the operational state of the circuit corresponds with the particular variety of invasive blood pressure being monitored. Other embodiments are also disclosed herein.

Some embodiments are depicted in the drawings, wherein like elements may be designated by like numerals throughout. In the following description, numerous specific details are provided for a thorough understanding of the embodiments described herein. However, those of skill in the art will recognize that one or more of the specific details may be omitted, or other methods, components, or materials may be used. Furthermore, the described features, operations, or characteristics may be combined in any suitable manner in one or more embodiments. It will also be readily understood that the order of the steps or actions of the methods described herein may be changed as would be apparent to those skilled in the art. Thus, any combination or order in the drawings or detailed description is for illustrative purposes only and is not meant to imply a required combination or order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Figure 1:
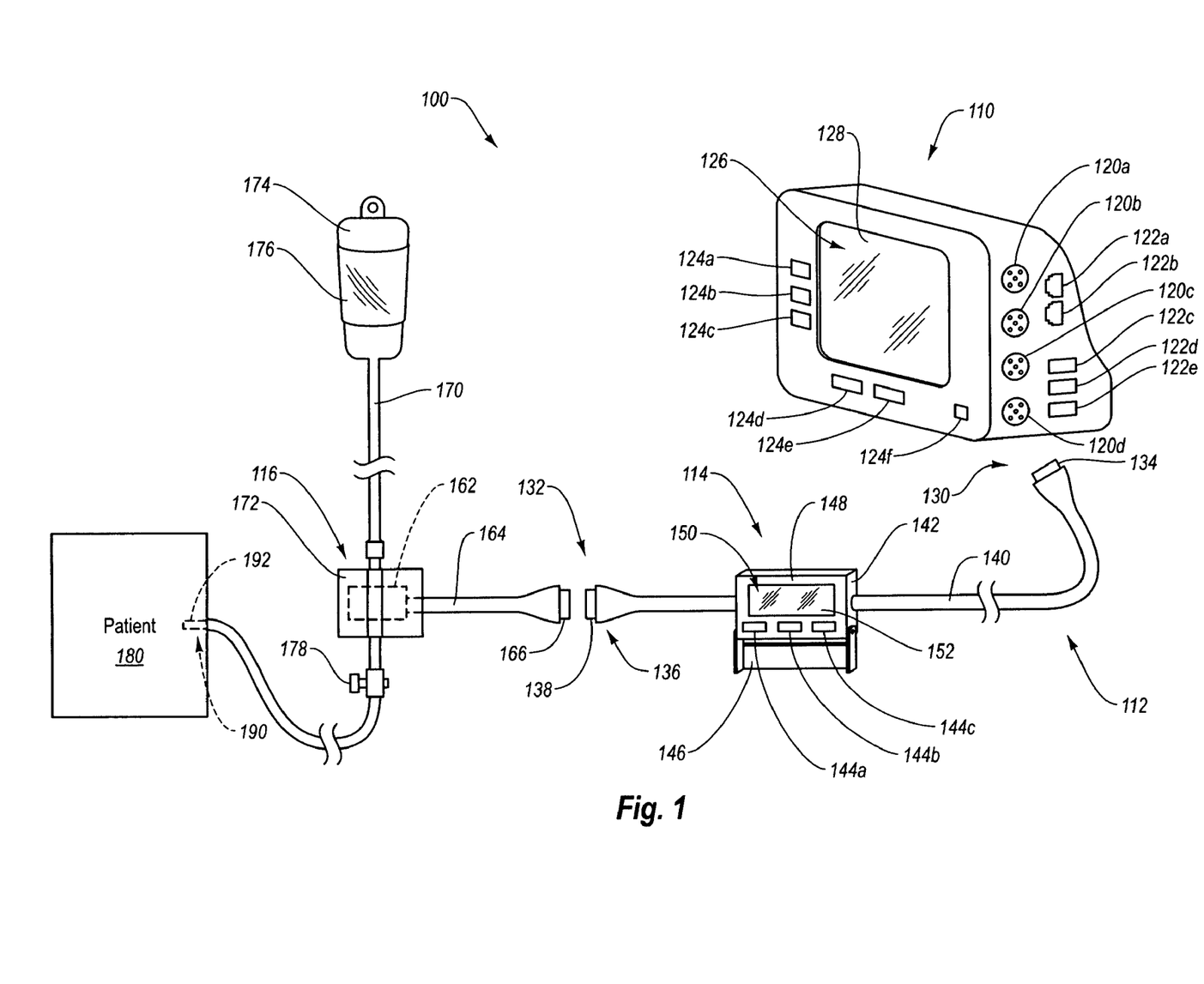
FIG. 1 is a partially exploded perspective view of an embodiment of a patient monitoring system including a monitor, cable, and control unit.

With reference to FIG. 1, in certain embodiments, a patient monitoring system 100 includes a patient monitor 110, a cable 112, a control unit 114, and a patient parameter sensor 116. The monitor 110 can include one or more connectors or ports 120 configured to communicate with the sensor 116. In some embodiments, the monitor 110 comprises one or more additional ports 122 that are configured to communicate with one or more additional sensors (such as, for example, other sensors described herein).

The monitor 110 can include one or more buttons or actuators 124 that are configured to effect one or more operations. In the illustrated embodiment, the actuators 124a, 124b, 124c, 124d, 124e comprise control buttons, which can, for example, be used to navigate through menus, make selections, or otherwise provide commands. The actuator 124f can comprise a power button.

The monitor 110 can include a display area 126 that is configured to display information in a visually perceivable format. For example, the display area 126 can include a screen 128 of any suitable variety, including those presently known and those yet to be devised. For example, the screen 128 can comprise a liquid crystal display (LCD) panel. In some embodiments, the screen 128 can be configured to receive information or otherwise interact with a medical practitioner. For example, the screen 128 can comprise a touch screen. In some embodiments, information received via one or more of the ports 120, 122 can be displayed on the screen 128.

The cable 112 can extend from a proximal end 130 to a distal end 132. In the illustrated embodiment, the cable 112 includes a connector 134 of any suitable variety at its proximal end 130. The connector 134 can be configured to be connected separately with any of the ports 120a, 120b, 120c,

120*d*. The cable 112 can include an electrical interface 136 at its distal end 132. In the illustrated embodiment, the electrical interface 136 comprises a connector 138 of any suitable variety. Extending between the connectors 134, 138 is a cable body 140. As discussed further below, the cable body 140 can include a plurality of electrical lines or electrical leads, which may be shielded and or otherwise encased.

The control unit 114 can be connected to the cable body 140. In the illustrated embodiment, the control unit 114 comprises a housing 142 configured to enclose or encase electrical components, and a portion of the cable body 140 extends into the housing 142 and is connected thereto. In other embodiments, the housing 142 is covered by or is integrally formed with a molding or an outer covering of the cable body 140. The illustrated embodiment of the control unit 114 further includes a plurality of control buttons or actuators 144, which are discussed further below.

The control unit 114 can include a cover 146 capable of rotating upward from the position shown in FIG. 1 so as to shield the actuators 144. The cover 146 can snap into place via a friction fit, or may be secured in the shielding position via any other suitable method. In further or other embodiments, the actuators 144 are recessed relative to a front face 148 of the housing 142 such that inadvertent contact with the actuators 144 may be reduced. In still further or other embodiments, actuation of a particular sequence or combination the actuators 144*a*, 144*b*, 144*c*, or a sustained actuation (e.g., depression) of one or more of the actuators 144*a*, 144*b*, 144*c* is required in order to effect a change of the control unit 114. Each of the mechanisms and methods discussed in this paragraph are examples of means for inhibiting accidental actuation of the actuators 144.

The control unit 114 can include a display 150 that is configured to provide visually perceivable information. Examples of information that may be displayed via the display 150 are discussed below. In some embodiments, the display 150 comprises a screen 152 of any suitable variety, including those presently known and those yet to be devised. For example, the screen 152 can comprise an LCD panel. In some embodiments, the screen 152 can be configured to receive information or otherwise interact with a medical practitioner. For example, in some embodiments, the screen 152 can comprise a touch screen, and in further embodiments, the functionality of one or more of the actuators 144 is provided by the touch screen.

In some embodiments, the control unit 114 is relatively small and can define a low profile. Although the illustrated embodiment of the control unit 114 is shaped substantially as a parallelepiped, other configurations are also possible. For example, the corners of the housing 142 can be smoothed or eliminated. In various embodiments, a maximum thickness of the housing 142 is within a range of from about 0.25 inches to about 1.0 inches, a maximum width of the housing 142 is within a range of from about 1.0 inches to about 2.0 inches, and a maximum height of the housing 142 is within a range of from about 0.5 inches to about 1.5 inches. In some embodiments, a viewable area of the screen 152 has a maximum width within a range of from about 0.5 inches to about 1.5 inches and a maximum height within a range of from about 0.25 inches to about 1.0 inches.

The control unit 114 can be closer to the distal end 132 of the cable 112 than it is to the proximal end 130. For example, in various embodiments, when the control unit 114 is electrically coupled with the sensor 116, the control unit 114 and the sensor 116 are within reach of each other such that the practitioner can position or adjust the sensor 116 and can manipulate the control unit 114 while the practitioner's feet remain in substantially the same position (e.g., without the practitioner walking between the sensor 116 to the control unit 114). In further embodiments, the control unit 114 can be positioned adjacent or near the sensor 116, or can be positioned adjacent or near the connector 138. In various further or other embodiments, the control unit 114 is at a distance of no greater than about 0.5 feet, no greater than about 1.0 feet, no greater than about 1.5 feet, no greater than about 2.0 feet, no greater than about 2.5 feet, no greater than about 3.0 feet, no greater than about 3.5 feet, or no greater than about 4.0 feet from one or more of the sensor 116, the distal end 132 of the cable 112, and the electrical interface 136 of the cable 112 (as measured along a length of the cable 112). In various embodiment, the control unit 114 is at a distance of no less than about 4.0 feet, no less than about 4.5 feet, no less than about 5.0 feet, no less than about 5.5 feet, no less than about 6.0 feet, or no less than about 6.5 feet from the proximal end 130 of the cable 112.

With continued reference to FIG. 1, the electrical interface 136 of the cable 112 can be configured to couple with the sensor 116. As used herein, the terms "couple" and "connect" can refer to one or more of a physical coupling or connection and an electrical coupling or connection. In some cases, the physical connection can be indirect. For example, in the illustrated embodiment, the sensor 116 comprises a pressure transducer 162, which is attached to a cable 164 that terminates in a connector 166. Coupling of the connectors 138, 166 can establish an electrical connection between the electrical interface 132 and the sensor 116, and further, can establish an indirect physical connection between the electrical interface 132 and the sensor 116, as the cable 164 physically separates the electrical interface 132 from the sensor 116. As discussed below, in other embodiments, the electrical interface 132 may be physically coupled directly to the sensor 116.

The pressure transducer 162 can interface with a pressurized fluid line 170. For example, in the illustrated embodiment, the pressure transducer 162 is mounted to a mounting plate 172 and is held in contact with the fluid line 170, which runs through or adjacent the mounting plate 170. Other suitable arrangements for the pressure transducer 162 are also possible. The source of pressurized fluid in the fluid line 170 can comprise, for example, a bag of saline solution 174 encompassed by a constricted sleeve 176.

The fluid line 170 can include a stopcock 178 in close proximity to the pressure transducer 162 that can be rotated so as to expose the fluid line 170 to atmospheric pressure (e.g., via a valve). When so positioned, the stopcock 178 can allow a baseline pressure of the fluid line 170 to be determined. For example, the pressure transducer 162 can be zeroed by actuating one or more of the actuators 144*a*, 144*b*, 144*c* of the control unit 114 when the fluid line 170 is exposed to atmospheric pressure, which can provide a reference pressure or baseline pressure against which fluctuations in the blood pressure of a patient 180 can be observed. Due to the proximity of the control unit 114 to the pressure transducer 162, in some embodiments, a practitioner can conveniently zero the pressure transducer 162 without a change in stance, such as, for example, without moving to a position within arm's length of one or more of the actuators 124*a*, 124*b*, 124*c*, 124*d*, 124*e*.

The fluid line 170 can be connected to a probing structure 190, such as, for example, a cannula 192 inserted in the vasculature of a patient. The cannula 192 can be of any suitable variety, and can be configured for insertion into the patient 180 in one or more specific positions. Those skilled in the art will recognize that a variety of placement options are available for the cannula 192, each of which can provide a different form of invasive blood pressure measurement. For example, the cannula 192 can be configured for insertion into the patient 180 so as to monitor the arterial blood pressure, central venous pressure, pulmonary arterial pressure, or intracranial pressure of the patient 180. Each separate placement of the cannula 192 can represent a different configuration of the sensor 116.

Figure 2:
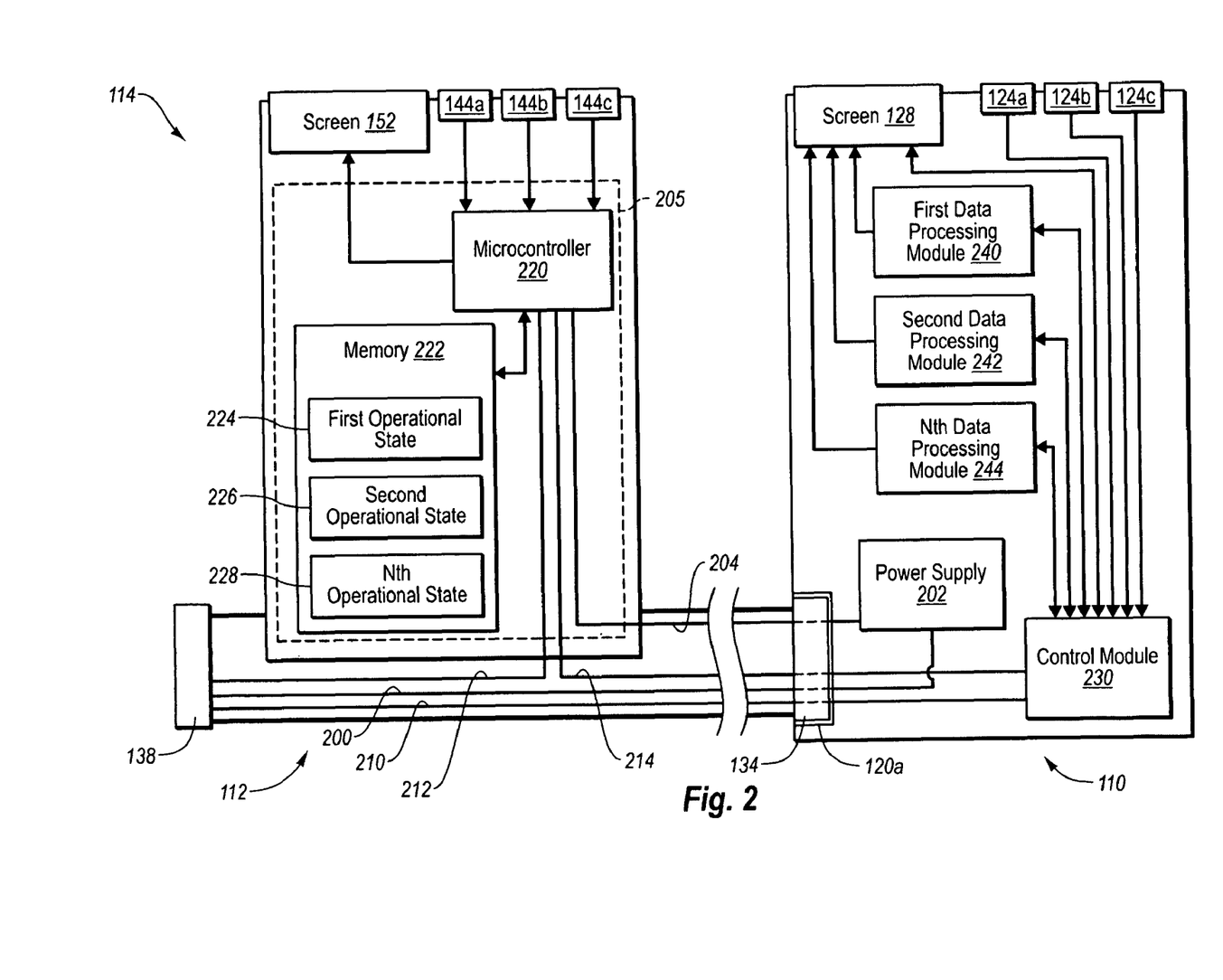
FIG. 2 is a simplified block diagram schematically illustrating the monitor and the cable of FIG. 1 in a coupled state.

FIG. 2 is a simplified block diagram schematically illustrating the monitor 110, the cable 112, and the control unit 114 of the system 100. The proximal connector 134 is shown coupled with the port 120a, and the distal connector 138 is shown in an uncoupled state. In certain embodiments, one or more power leads 200 extend between the proximal and distal connectors 134, 138. In some embodiments, the one or more power leads 200 can be configured to provide electrical power to the sensor 116 from a power supply 202 of the monitor 110. In other embodiments, the sensor 116 is configured to operate without power from the monitor 110, and the cable 112 may not include the one or more power leads 200.

The cable 112 can include one or more power leads 204 configured to couple an electrical circuit 205 of the control unit 114 with the power supply 202 of the monitor 110. The one or more power leads 204 can extend between the proximal connector 134 and the circuit 205.

One or more communication leads 210 can extend between the proximal and distal connectors 134, 138. The one or more communication leads 210 can be configured to transmit information between the sensor 116 and the monitor 110. In some embodiments, the cable 112 includes one or more communication leads 212 extending between the distal connector 138 and the circuit 205. Accordingly, in some embodiments, the circuit 205 can communicate directly with the sensor 116. In other embodiments, the circuit 205 communicates with the sensor 116 only indirectly (e.g., via the monitor 110), and thus may not include the communication lead 212.

The cable 112 can include one or more communication leads 214 extending between the proximal connector 134 and the circuit 205. As further discussed below, the circuit 205 can be configured to communicate with the monitor 110 via the communication lead 214 when the proximal connector 134 is connected to the monitor 110.

The circuit 205 can comprise a microcontroller 220 and/or other microelectronic components. The microcontroller 220 can be configured to receive input from the actuators 144a, 144b, 144c, the monitor 110 (via the one or more communication leads 214), and/or a memory device or memory 222. The microcontroller 220 can be configured to output information to the screen 152, and can be configured to store information in the memory 222 and/or access information stored in the memory 222. Although the microcontroller 220 and the memory 222 are shown as separate components in the schematic diagram shown in FIG. 2, in some embodiments, the memory 222 can be integral with the microcontroller 220.

The memory 222 can be configured to store a variety of information regarding the cable 112, and the information can be updated or otherwise altered via the microcontroller 220. In some embodiments, the information stored in the memory 222 comprises information regarding the cable 112 itself, such as its manufacturer, date of manufacture, date of first operation, most recent period of active usage, cumulative total time of active usage, expiration date, settings from previous uses, and/or other information. In further or other embodiments, the memory 222 can store information related to or unrelated to the operation of the cable 112, such as the scale settings for a patient parameter that may be or is being monitored (e.g., pressure, temperature, or voltage), alarm limits for a particular monitoring event, information regarding the patient 180 being monitored, information regarding the pressurized saline bag 174, etc. Additionally, in some embodiments, information can be erased from the memory 222. For example, information regarding the identity of a patient can be erased upon discharge of the patient. In some embodiments, a user may select a preferred language in which to display stored information (or other information) via the screen 152.

In some embodiments, the memory 222 can store information regarding different operational states of the circuit 220, which correspond with different operational states of the cable 112. For example, as previously discussed, a given sensor 116 (or different sensors 116) can operate in a variety of different sensor configurations, depending on the placement of a probing structure 190 relative to a patient 180. Thus, for example, the transducer 162, and hence the cable 112 when it is coupled to the transducer, can be configured to operate in any of an arterial blood pressure sensing configuration, a central venous pressure sensing configuration, a pulmonary arterial pressure sensing configuration, an intracranial pressure sensing configuration, or other pressure sensing configuration. Particular information regarding each possible configuration in which a sensor 116 (and cable 112) may operate can be stored in the memory 222. For example, information can be stored regarding one or more of a first operational state 224, a second operational state 226, and any additional operational state up to and including an Nth operational state (where "N" represents any suitable integer). Each operational state stored in the memory 222 can also be referred to as a channel.

Information regarding an operational state 224, 226, 228 can include a label or text that is representative of that state (e.g., "ART" for arterial pressure or "ICP" for intracranial pressure), which can be displayed via the screen 152 when the operational state has been selected. The information likewise can include instructions that can be delivered to the monitor 110 via the communication lead 214 upon selection of an operational state.

An operational state 224, 226, 228 can be selected via actuation of one or more of the actuators 144a, 144b, 144c. Likewise, the actuation of one or more of the actuators 144a, 144b, 144c can be used to transition among the operational states 224, 226, 228. Reference herein to actuating one or more of the actuators 144a, 144b, 144c can indicate that one of the actuators may be actuated, two of the actuators may be actuated in combination (e.g., in series, in tandem, etc.), or any other suitable actuation combination is possible to achieve the stated action. In various embodiments, one or more of the actuators 144a, 144b, 144c can be actuated to transition the circuit 205 among two or more, three or more, four or more, or any other suitable number of operational states. Selection of an operational state 224, 226, 228 can result in the circuit 205 operating in the selected operational state. For example, upon the selection of an operational state, the microcontroller 220 can deliver instructions regarding the operational state to a control module 230 of the monitor 110.

In other or further embodiments, one or more of the actuators 144a, 144b, 144c can be actuated to effect a change in the circuit 205 other than to transition among the operational states 224, 226, 228. For example, as discussed above one or more of the actuators 144a, 144b, 144c can be actuated to "zero" or otherwise calibrate a patient parameter sensor 116 (e.g., the transducer 162). Another example includes instigating a diagnostic check of the cable, such as to ensure that none of the leads 200, 204, 210, 212, 214 contain any discontinuities. Yet another example includes actuating one or more of the actuators 144a, 144b, 144c to access, alter, or erase information stored in the memory 222, or to store information in the memory 222.

In some embodiments, the monitor 110 is configured to process information received via the port 120a in a mode that corresponds with an operational state of the cable 112 and the circuit 205. In the illustrated embodiment, the monitor 110 comprises a first data processing module 240, a second data processing module 242, and additional data processing modules up to and including an Nth data processing module 244 (where "N" represents any suitable integer). When the monitor 110 processes information received by the port 120a via one of the data processing modules 240, 242, 244, the monitor 110 can be referred to as operating in an operational mode associated with that data processing module 240, 242, 244. Stated otherwise, each data processing module 240, 242, 244 can define a separate channel of the monitor 110, and the channels of the monitor can correspond with the channels of the circuit 205. In various embodiments, the monitor 110 can be configured to operate in one or more, two or more, three or more, four or more, or any other suitable number of operational modes or channels.

Each data processing module 240, 242, 244 can include an algorithm or other data processing system suitable for a particular sensor configuration. Thus, for example, the first data processing module 240 may be particularly suited to process information regarding arterial pressure, whereas the second data processing module 242 may be particularly suited to process information regarding intracranial pressure. The control module 230 is configured to receive instructions regarding a selected operational state of the circuit 205 and, based on this information, to automatically route information received via the one or more communication leads 210 to the appropriate or associated data processing module 240, 242, 244. The processed information can be displayed via the screen 128.

With continued reference to FIG. 2, the ports 120a, 120b, 120c, 120d can be substantially interchangeable. For example, in some embodiments, the schematic diagram of the monitor 110 would be substantially the same if the port 120a were replaced with any of the ports 120b, 120c, 120d (see FIG. 1). Accordingly, if the cable 112 were disconnected from the port 120a (e.g., from the configuration shown in FIG. 2) and connected with any of the ports 120b, 120c, 120d, the monitor 110 would automatically select a data processing module 240, 242, 244 corresponding with the operational state of the circuit 205. The monitor 110 thus can automatically conform to or synchronize with one or more cables 112 connected thereto, and can automatically process information received via the ports 120a, 120b, 120c, 120d in one or more operational modes that correspond with the operational states of the one or more cables 112 (or their associated circuits 205) respectively. In some embodiments, selection of a data processing module 240 occurs substantially simultaneously with connection of a cable 112 to the monitor 110.

In certain embodiments, the monitor 110 can access information stored in the memory 222 via the control module 230, and can display the same via the screen 128. Likewise, in some embodiments, the actuators 124 can be used to access, alter, delete, or store information in the memory 222.

Figure 3:
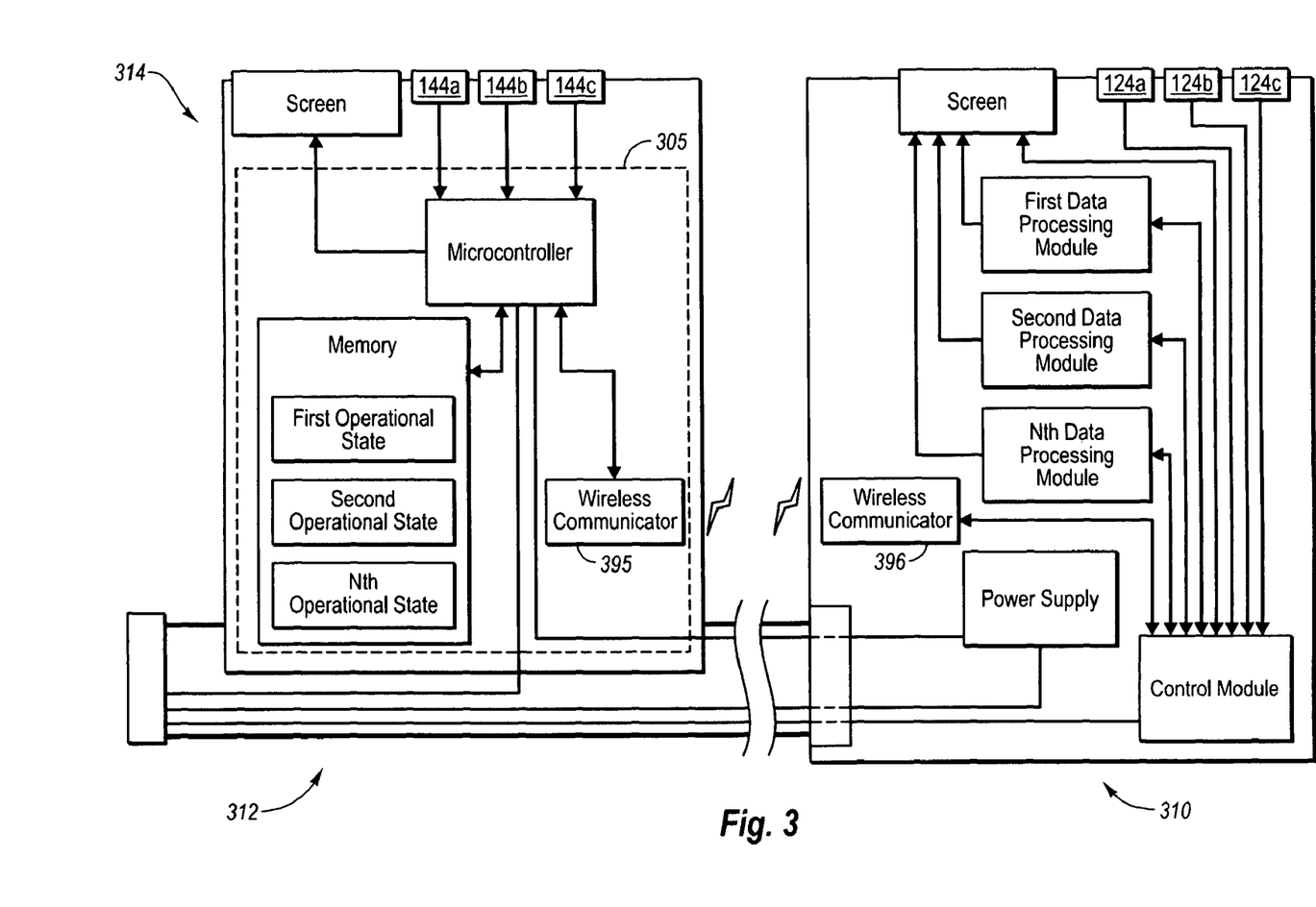
FIG. 3 is a simplified block diagram schematically illustrating other embodiments of a monitor, a cable, and control unit in a coupled state.

FIG. 3 illustrates another embodiment of a monitor 310 connected with another embodiment of a cable 312 that includes an embodiment of a control unit 314. The monitor 310, the cable 312, and the control unit 314 can resemble the monitor 110, the cable 312, and the control unit 114, respectively, thus like features are represented by like reference numerals, with the leading digit incremented to "3." The control unit 314 can include a circuit 305 that includes a wireless communicator 395. The monitor 310 can include a wireless communicator 396 configured to communicate with the wireless communicator 395. Comparison of FIGS. 2 and 3 illustrates that the wireless communicators 395, 396 can replace the communication lead 214. Any suitable variety of wireless communicators 395, 396 are possible, including RFID systems, Bluetooth systems, infrared systems, etc.

Figure 4:
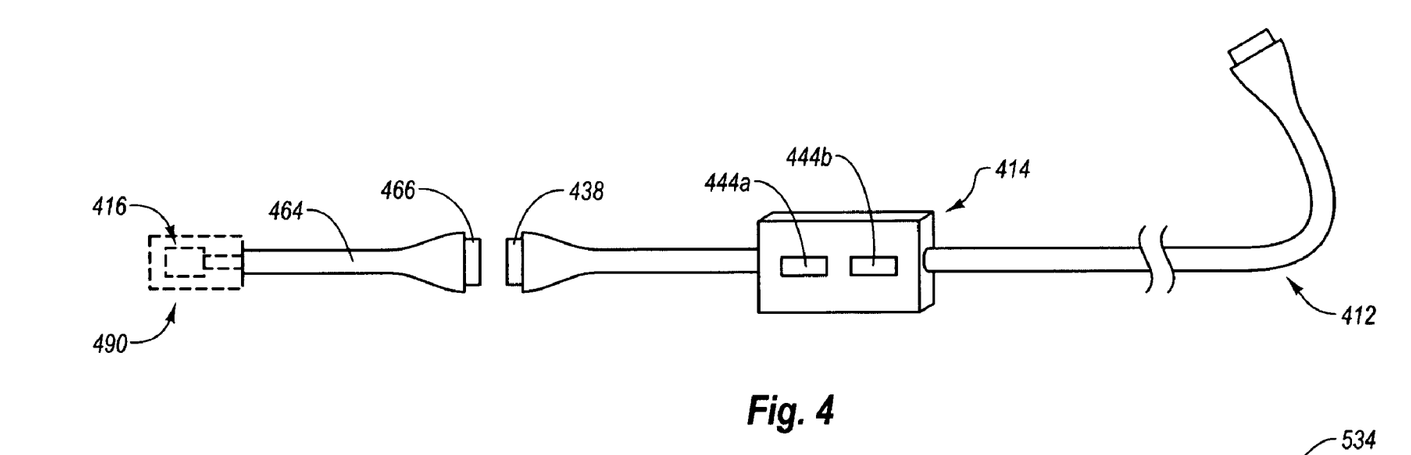
FIG. 4 is a perspective view of another embodiment of a cable that includes another embodiment of a control unit and an embodiment of a patient parameter sensor with which the cable is configured to couple.

FIG. 4 illustrates another embodiment of a cable 412 that includes an embodiment of a control unit 414. The cable 412 can be selectively connected with a cable 464, which can include a proximal connector 466, a probing structure 490, and a sensor 416. The cable 412 and components thereof can resemble the cables 112, 312 and components thereof, and the cable 464 and components thereof can resemble the cable 164 and components thereof, thus like features are represented by like reference numerals, with the leading digit incremented to "4."

The illustrated control unit 414 includes two actuators 444a, 444b. As with the actuators 144 of the control unit 114, more or few actuators 444 are possible, and may vary depending on the desired functionality of the control unit 414. In the illustrated embodiment, the actuator 444a is configured to select a channel or operational state of the cable 412, and the actuator 444b is configured to zero the sensor 416 and/or instigate a sensing event via the sensor 416.

The control unit 414 also differs from the embodiment of the control unit 114 illustrated in the FIGS. 1 and 2 in that it does not include a display. In some embodiments, the control unit 414 is configured to communicate with a monitor (such as the monitors 110, 310 discussed above) such that a screen of the monitor can be used to display information supplied by the control unit 414. Thus, for example, a channel selected via the actuator 444a can be displayed on a screen of the monitor, rather than on the control unit 414 itself.

In the illustrated embodiment, the sensor 416 is integral with the probing structure 490. For example, in some embodiments the sensor 416 and the probing structure 490 comprise a temperature probe (e.g., a probe that includes a thermistor). Other types and arrangements are possible for the sensor 416 and the probing structure 490. For example, in some embodiments, a cuff system for measuring noninvasive blood pressure can comprise the probing structure 490 and the sensor 416. Other arrangements of the probing structure 490 and the sensor 416 can be suitable for measuring patient parameters such as, for example, respiration activity, cardiac activity, brain activity, etc.

Figure 5:
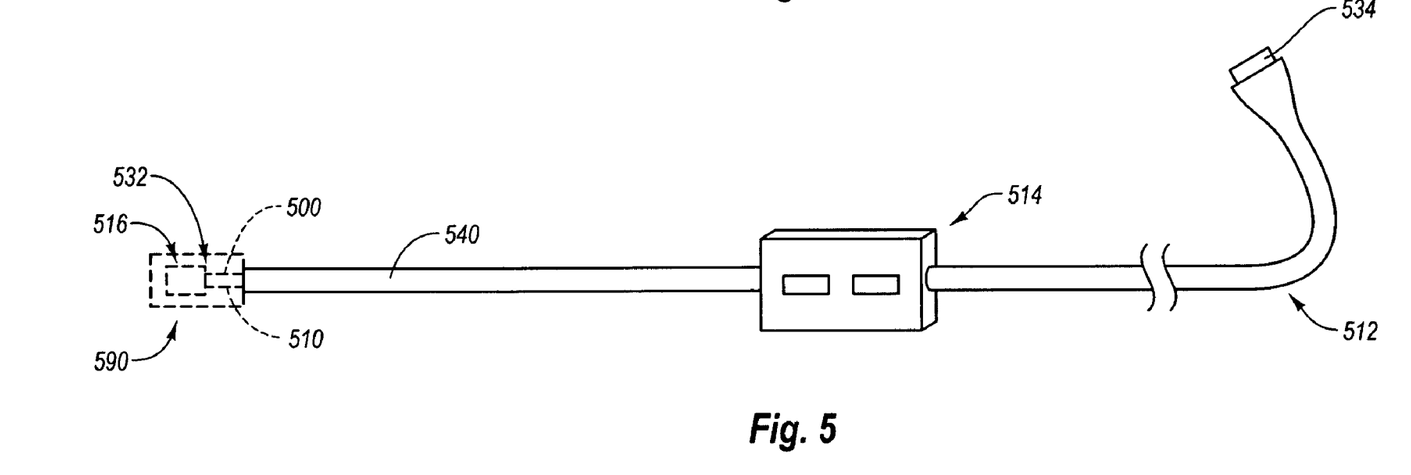
FIG. 5 is a perspective view of another embodiment of a cable that includes another embodiment of a control unit and is integrally connected with an embodiment of a patient parameter sensor.

FIG. 5 illustrates another embodiment of a cable 512 that includes an embodiment of a control unit 514. The cable 512 and components thereof can resemble the cables 112, 312, 412 and components thereof, thus like features are represented by like reference numerals, with the leading digit incremented to "5." In the illustrated embodiment, the cable 512 includes a cable body 540 coupled with the probing structure 590 in a direct physical engagement. The cable body 540 can include a power lead 500 and a communication lead 510, each of which can be coupled with a connector 534 at a proximal end thereof and coupled with a sensor 516 at a distal end thereof. An electrical interface 532 of the cable 512 thus can include the distal ends of the power lead 500 and the communication lead 510.

Figure 6:
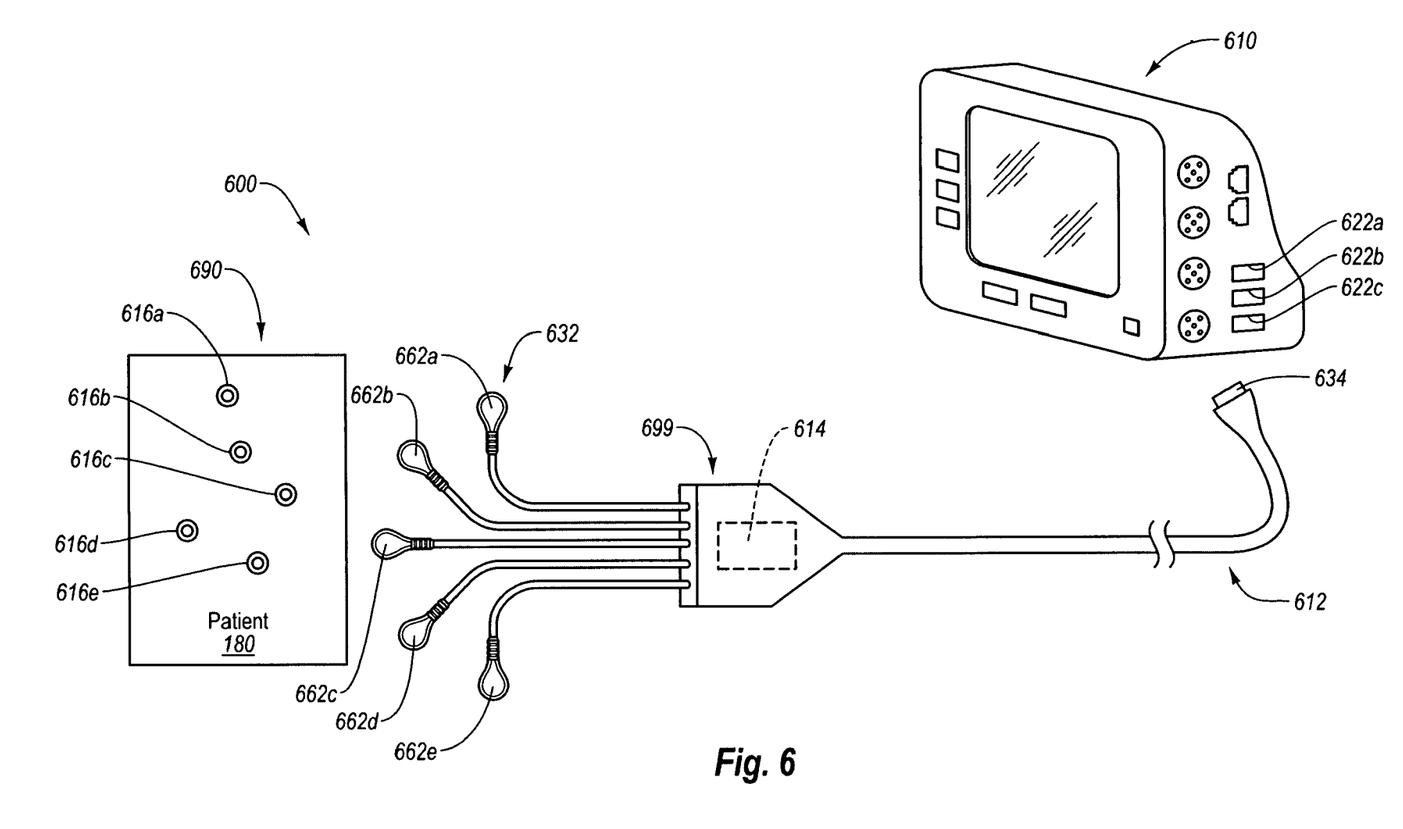
FIG. 6 is a partially exploded perspective view of another embodiment of a patient monitoring system including another embodiment of a monitor, cable, and control unit.

FIG. 6 illustrates another embodiment of a patient monitoring system 600 such as the patient monitoring system 100 discussed above. Like features are represented by like numerals, with the leading digit incremented to "6." The system 600 can include a monitor 610 and a cable 612. Embodiments of the monitor 610 can include features of one or more of the monitors 110, 310 discussed above. The monitor 610 can include one or more ports 622a, 622b, 622c.

The cable 612 can be particularly suited for use in electrocardiography, and can comprise multiple leads 662 that extend from a yoke 699. As one skilled in the art will appreciate, the cable 612 can comprise more of fewer leads 662 than those shown in FIG. 6. The distal ends of the leads 662 can define an electrical interface 632 of the cable 612. The electrical interface 632 can be configured to couple with a probing structure 690, which can comprise a plurality of sensors 616 (e.g., electrodes) that can be coupled to the patient 180.

The cable 612 can comprise a control unit 614 such as any of the control units 114, 314, 414, 514 discussed above. In particular, features of any of the previously discussed control units can be incorporated into the control unit 614, and vice versa. In the illustrated embodiment, the control unit 614 is completely embedded within the cable 612. In some embodiments, the control unit 614 does not include a screen, and in further embodiments, does not include any actuators.

Figure 7:
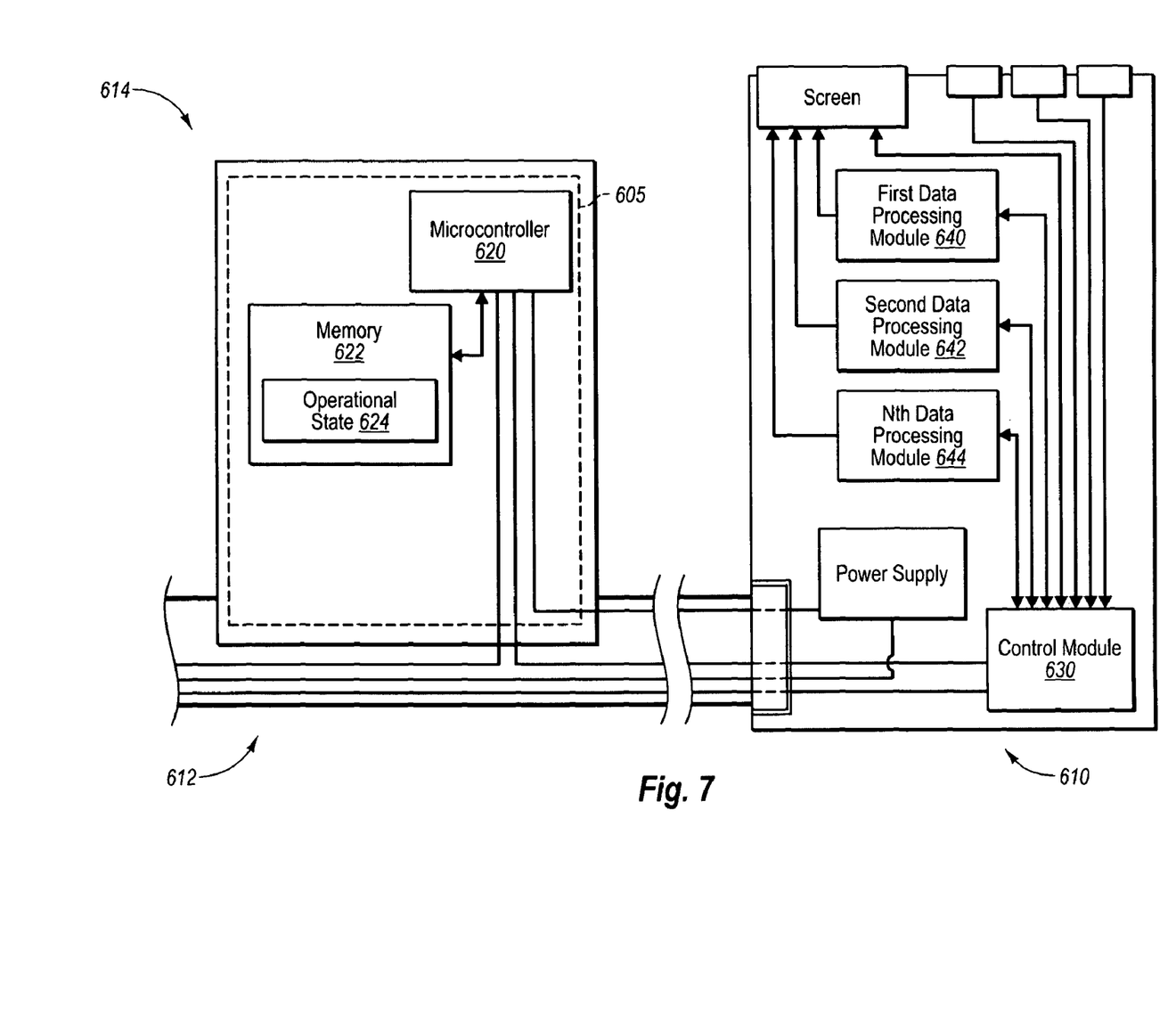
FIG. 7 is a simplified block diagram schematically illustrating the monitor and the cable of FIG. 6 in a coupled state.

FIG. 7 is a simplified block diagram schematically illustrating the monitor 610, the cable 612, and the control unit 614 of FIG. 6. Like the monitors 110, 310, the monitor 610 can have one or more data processing modules. In the illustrated embodiment, the monitor 610 includes a first data processing module 640, a second data processing module 642, and an Nth data processing module 644. Each data processing module 640, 642, 644 can be configured to operate with a corresponding operational state of a cable. The monitor 610 can also include a control module 630 such as the control module 230.

The control unit 614 can include a circuit 605, which may include one or more of a microcontroller 620 and a memory device 622. In some embodiments, a microcontroller is not used.

In the illustrated embodiment, the cable 612 includes a single operational state 624, which may be stored in the memory device 622. The operational state 624 can include stored instructions regarding operation of the cable 612, as well as any other suitable information (such as that discussed above with respect to the cable 112). Additionally, the stored instructions can include, for example, information regarding the number of leads 662 possessed by the cable 612.

Upon coupling the cable 612 with the monitor 610, the control module 630 can access information regarding the operational state 624, and can automatically transition the monitor 610 into an operational mode that employs the first data processing module 640 to process information received via the leads 662 of the cable 612. Stated otherwise, based on the information received from the circuit 605, the monitor 610 can automatically select an appropriate channel for processing information obtained via the cable 612.

As previously mentioned, features described with respect to of any of the cables 112, 312, 412, 512, and 612 can be combined in any suitable arrangement. The same is true of other similarly numbered components or features, such as the control units 114, 314, 414, 514 and the monitors 110, 310, 610. Additionally, sub-combinations of the disclosed features are also contemplated, and may represent additional embodiments.

For example, with reference again to FIGS. 1 and 2, in certain embodiments, the cable 112 does not communicate information regarding its operational state to the monitor 110 when the connector 134 is coupled with the port 120a. For example, in some embodiments, the cable 112 does not include the communication lead 204. The control unit 114 can otherwise be substantially the same as that depicted in FIG. 2, and can include one or more of the operational states 224, 226, 228. Transition among the operational states 224, 226, 228 can be effected by actuation of one or more of the actuators 144a, 144b, 144c. Each of the operational states 224, 226, 228 can include information, such as textual information or other data, regarding a specific sensor configuration with which the cable 112 is configured to operate. For example, one operational state 224 can include instructions for displaying the text "ART" via the screen 152 to represent that the cable 112 is being used to monitor arterial blood pressure, whereas another operational state 226 can include instructions for displaying the text "ICP" via the screen 152 to represent that the cable 112 is being used to monitor intracranial pressure. However, the operational states 224, 226, 228 may be devoid of instructions for switching the monitor 110 among its various operational modes. The operational modes can instead be selected via one or more of the actuators 124a, 124b, 124c of the monitor 110 (e.g., the actuators 124a, 124b, 124c can be used to cycle through the data processing modules 240, 242, 244).

In further or other embodiments, information other than information regarding the operational state of the cable 112 can be stored in the memory 222 and/or displayed via the screen 152. Non-limiting examples of such other information that can be stored and/or displayed are provided elsewhere in this disclosure.

As another example, in certain embodiments, the cable 112 includes the communication lead 204, but the control unit 114 is devoid of actuators 144a, 144b, 144c. In some embodiments, the control unit 114 can function substantially as a follower or echo device relative to the monitor 110. For example, an operational mode of the monitor 110 can be selected via one or more of the actuators 124a, 124b, 124c (e.g., a data processing module 240, 242, 244 can be selected). The control unit 114 can be configured to receive information from the monitor 110 regarding the selected operational mode, and can automatically select a corresponding operational state 224, 226, 228. In other or further embodiments, information displayed via the screen 150 of the control unit 114 can be selectively controlled via interaction with the monitor 110, such as by actuating one or more of the actuators 124a, 124b, 124c.

It will be understood by those having skill in the art that many changes may be made to the details of the above-described embodiments without departing from the underlying principles of the present invention. The scope of the present invention should, therefore, be determined only by the following claims. Recitation in the claims of the term "either" does not necessarily refer to two exclusive options, and may include within its scope more options than those explicitly listed. Recitation in the claims of the term "first" with respect to a feature or element does not necessarily imply the existence of a second or additional such feature or element. Elements recited in means-plus-function format are intended to be construed in accordance with 35 U.S.C. § 112¶6.

What is claimed is:

1. A patient monitoring system comprising:
   a patient monitor comprising a first port, wherein the patient monitor is configured to process information received via the first port in any of two or more operational modes; and
   a cable comprising:
      a connector configured to couple with the first port;
      an electrical interface configured to communicate with a patient parameter sensor;

a circuit configured to provide information regarding any of at least two operational states of the cable, wherein each operational state of the cable corresponds with a separate operational mode of the patient monitor; and an actuator electrically coupled with the circuit, wherein the actuator is configured to transition the circuit among the at least two operational states, wherein, for each operational state, the cable is configured to obtain information regarding a patient parameter from a patient sensor via the electrical interface and is configured to deliver the information to the patient monitor via the first port, and wherein the circuit is configured to communicate an operational state of the cable to the patient monitor, such that selection of an operational state of the circuit via the actuator automatically causes the patient monitor to operate in the corresponding operational mode so as to process the information regarding the patient parameter.

2. The patient monitoring system of claim 1, wherein the circuit is configured to store information received from the patient monitor.

3. The patient monitoring system of claim 1, wherein the actuator is closer to the electrical interface than it is to the connector.

4. The patient monitoring system of claim 1, wherein the cable further comprises a display configured to provide a visually perceivable representation of a current operational state of the circuit.

5. The patient monitoring system of claim 2, wherein the patient monitor further comprises a second port and the connector is configured to separately couple with either the first port or the second port, wherein the monitor is configured to process information received via the second port in any of two or more operational modes, and wherein the monitor is configured to automatically process information received via the second port in an operational mode that corresponds with an operational state of the cable as communicated by the circuit.

6. The patient monitoring system of claim 1, wherein the cable comprises a communication lead coupled with the connector and the circuit, and wherein the circuit is configured to communicate an operational state of the cable to the patient monitor via the communication lead.

7. The patient monitoring system of claim 1, wherein the circuit comprises a wireless communicator, and wherein the circuit is configured to communicate an operational state of the cable to the patient monitor via the wireless communicator.

8. The patient monitoring system of claim 1, wherein the patient monitor comprises two or more data processing modules, and wherein one of the data processing modules is automatically selected for processing the information received from the cable based on the operational state of the cable.

9. The patient monitoring system of claim 1, further comprising a sensor connected to the electrical interface of the cable.

10. A cable comprising:
a first connector configured to electrically couple with a patient monitor;
an electrical interface configured to communicate with a patient parameter sensor;
a cable body extending between the first connector and the electrical interface, the cable body comprising one or more leads that electrically couple the first connector with the electrical interface;

a circuit configured to transition among a plurality of operational states, wherein each operational state corresponds to a different sensor configuration; and a first actuator electrically coupled with the circuit, wherein the first actuator is configured to be actuated so as to transition the circuit among the plurality of operational states, wherein, in each of the plurality of operational states, the cable is configured to deliver information from the electrical interface to the first connector such that, when the electrical interface is coupled with a patient parameter sensor and the first connector is coupled with a patient monitor, the cable can transmit information obtained from the patient parameter sensor to the patient monitor; and wherein the circuit is configured to communicate an operational state of the cable to the patient monitor, such that selection of an operational state of the circuit via the first actuator automatically causes the patient monitor to operate in the corresponding operational mode so as to process the information regarding the patient parameter.

11. The cable of claim 10, further comprising a display electrically coupled with the circuit.

12. The cable of claim 11, wherein the display comprises a screen that is configured to provide a textual representation of a current operational state of the circuit.

13. The cable of claim 11, wherein the display and the first actuator are attached to the cable body at a position that is closer to the electrical interface than it is to the first connector.

14. The cable of claim 10, further comprising a power lead extending between the first connector and the circuit, wherein the power lead is configured to deliver electrical power to the circuit when the first connector is coupled with a monitor.

15. The cable of claim 10, further comprising a communication lead extending between the first connector and the circuit, wherein the circuit is configured to communicate with a monitor via the communication lead when the first connector is connected to the monitor.

16. The cable of claim 10, wherein the circuit comprises a wireless communicator configured to transmit information regarding the operational state of the circuit.

17. The cable of claim 10, wherein the circuit comprises a memory configured to store therein information regarding the cable that is received from a patient monitor via the first connector.

18. The cable of claim 10, further comprising a second actuator electrically coupled with the circuit, wherein actuation of one of the first and second actuators or actuation of a combination of the first and second actuators is configured to effect a change other than a transition among the operational states of the circuit.

19. The cable of claim 18, wherein said change other than a transition among the operational states of the circuit comprises one or more of zeroing a patient parameter sensor that is coupled with the electrical interface, instigating a measurement of blood pressure via a noninvasive blood pressure sensor that is coupled with the electrical interface, instigating a diagnostic check of the cable, accessing information stored in a memory portion of the circuit, altering information stored in a memory portion of the circuit, erasing information stored in a memory portion of the circuit, and storing information in a memory portion of the circuit.

20. The cable of claim 10, further comprising a communication lead extending between the electrical interface and the first connector, wherein the communication lead bypasses the circuit so as not to be influenced thereby such that transition of the circuit from one operational state to another does not affect transmission of information along the communication lead.

21. The cable of claim 10, wherein the electrical interface comprises a second connector configured to electrically couple with a patient parameter sensor.

22. The cable of claim 10, wherein the electrical interface comprises one or more ends of the one or more leads.

23. The cable of claim 10, further comprising a patient parameter sensor permanently coupled with the electrical interface.

24. The cable of claim 23, wherein the patient parameter sensor comprises one of a pressure transducer, a temperature sensor, and an electrocardiogram electrode.

25. The cable of claim 10, wherein said sensor configuration corresponds with a position of a probing structure relative to a patient.

26. A cable comprising:
a connector configured to electrically couple with a patient monitor;
an electrical interface configured to communicate with a pressure transducer;
a cable body extending between the first connector and the electrical interface, the cable body comprising one or more leads that electrically couple the first connector with the electrical interface;
a circuit configured to transition among a two or more operational states, wherein the connector is electrically coupled with the electrical interface such that, in each of the two or more operational states, information obtained from the pressure transducer via the electrical interface is delivered to the connector; and
an actuator electrically coupled with the circuit, wherein the actuator is attached to the cable body at a position that is closer to the electrical interface than it is to the connector, and wherein the circuit is configured to zero a patient monitor relative to a pressure transducer when the cable is connected with both the patient monitor and the pressure transducer and the actuator is actuated,
wherein the circuit is configured to communicate an operational state of the cable to the patient monitor, such that selection of an operational state of the circuit via the actuator automatically causes the patient monitor to operate in the corresponding operational mode so as to process the information regarding the patient parameter.

27. A cable comprising:
a connector configured to electrically couple with a patient monitor;
an electrical interface configured to communicate with a noninvasive blood pressure sensor;
a cable body extending between the first connector and the electrical interface, the cable body comprising one or more leads that electrically couple the first connector with the electrical interface;
a circuit configured to transition among a two or more operational states, wherein the connector is electrically coupled with the electrical interface such that, in each of the two or more operational states, information obtained from the noninvasive blood pressure sensor via the electrical interface is delivered to the connector; and
an actuator electrically coupled with the circuit, wherein the actuator is attached to the cable body at a position that is closer to the electrical interface than it is to the connector, and wherein the circuit is configured to instigate measurement of blood pressure via the noninvasive blood pressure sensor upon actuation of the actuator, wherein the circuit is configured to communicate an operational state of the cable to the patient monitor, such that selection of an operational state of the circuit via the actuator automatically causes the patient monitor to operate in the corresponding operational mode so as to process the information regarding the patient parameter.

28. A cable comprising:
a connector configured to electrically couple with a patient monitor;
an electrical interface configured to communicate with a patient parameter sensor;
a cable body extending between the first connector and the electrical interface;
a circuit configured to transition among a two or more operational states, wherein the connector is electrically coupled with the electrical interface such that, in each of the two or more operational states, information obtained from the patient parameter sensor via the electrical interface is delivered to the connector;
a screen electrically coupled with the circuit, wherein the screen is configured to provide a visually perceivable display based on information received from the circuit; and
one or more actuators coupled with the circuit, wherein actuation of the one or more actuators is configured to change the visually perceivable display provided by the screen and is configured to transition the circuit among the two or more operational states,
wherein the circuit is configured to communicate an operational state of the cable to the patient monitor, such that selection of an operational state of the circuit via the one or more actuator automatically causes the patient monitor to operate in the corresponding operational mode so as to process the information regarding the patient parameter.

29. The cable of claim 28, wherein the circuit further comprises a memory, wherein the actuator is configured to cause information stored in the memory to be displayed via the screen.

30. The cable of claim 28, wherein said information comprises data regarding one or more of a manufacturer of the cable, a date of manufacture of the cable, a date of first operation of the cable, a most recent period of active usage of the cable, a cumulative total time of active usage of the cable, an expiration date of the cable, settings from previous uses of the cable, scale settings of a patient parameter monitored via the cable, alarm limits, and a patient with whom the cable is used.

31. The patient monitoring system of claim 1, wherein the cable further comprises a communication lead extending between the connector and the electrical interface, wherein the communication lead bypasses the circuit so as not to be influenced thereby such that transition of the circuit from one operational state to another does not affect transmission of information along the communication lead.

32. The cable of claim 26, further comprising an additional actuator electrically coupled with the circuit, wherein the additional actuator is configured to transition the circuit among the operational states.

33. The cable of claim 27, further comprising an additional actuator electrically coupled with the circuit, wherein the additional actuator is configured to transition the circuit among the operational states.

* * * * *